(12) United States Patent
Schuller

(10) Patent No.: US 10,226,378 B2
(45) Date of Patent: Mar. 12, 2019

(54) DISPOSABLE THERMAL REGULATION APPARATUS

(71) Applicant: Carmen Schuller, New York, NY (US)

(72) Inventor: Carmen Schuller, New York, NY (US)

(73) Assignee: Carmen Schuller, New York, NY (US)

( * ) Notice: Subject to any disclaimer, the term of this patent is extended or adjusted under 35 U.S.C. 154(b) by 181 days.

(21) Appl. No.: 14/192,460

(22) Filed: Feb. 27, 2014

(65) Prior Publication Data

US 2014/0243940 A1 Aug. 28, 2014

Related U.S. Application Data

(60) Provisional application No. 61/770,895, filed on Feb. 28, 2013, provisional application No. 61/845,136, filed on Jul. 11, 2013.

(51) Int. Cl.
| | |
|---|---|
| *A61F 7/10* | (2006.01) |
| *A61F 7/03* | (2006.01) |
| *A61F 7/00* | (2006.01) |
| *A61F 7/02* | (2006.01) |

(52) U.S. Cl.
CPC ............. *A61F 7/106* (2013.01); *A61F 7/034* (2013.01); *A61F 2007/0008* (2013.01); *A61F 2007/0095* (2013.01); *A61F 2007/0271* (2013.01); *A61F 2007/0287* (2013.01)

(58) Field of Classification Search
CPC ..... A61F 2007/0271; A61F 7/03; A61F 7/106
See application file for complete search history.

(56) References Cited

U.S. PATENT DOCUMENTS

| | | | |
|---|---|---|---|
| 4,382,446 A * | 5/1983 | Truelock | A61F 7/03 607/110 |
| 5,785,980 A | 7/1998 | Mathewson | |
| 5,897,582 A * | 4/1999 | Agnatovech | A61F 7/10 607/109 |
| 6,030,412 A * | 2/2000 | Klatz | A61F 7/00 607/104 |
| 2004/0138729 A1* | 7/2004 | Ladmer | A61F 7/02 607/109 |
| 2004/0186541 A1* | 9/2004 | Agarwal | A61F 7/03 607/114 |
| 2006/1001895 | 1/2006 | Guillon et al. | |
| 2007/0106352 A1* | 5/2007 | Carstens | A41D 13/1161 607/112 |
| 2007/0150033 A1* | 6/2007 | Johnson | A61F 7/106 607/114 |

(Continued)

FOREIGN PATENT DOCUMENTS

| | | | | |
|---|---|---|---|---|
| WO | WO 2012/162140 | 11/2012 | | |
| WO | WO 2012162140 A2 * | 11/2012 | ........... | A43B 3/0005 |

*Primary Examiner* — Joseph Stoklosa
*Assistant Examiner* — Adam Avigan
(74) *Attorney, Agent, or Firm* — Leason Ellis LLP

(57) ABSTRACT

The present invention is directed to a thermo-regulation device for treating an area with in need of thermal regulation. The invention includes a device configured to be fitted over an area in need of thermal regulation; wherein a plurality of cells are integral to the covering body, each cell is equipped with at least one of a plurality of reactants. Each cell of the present invention is in one configuration joined to a neighboring cell by a destructible barrier. The reactants are configured to produce a thermal event when combined with at least one other reactant.

5 Claims, 5 Drawing Sheets

(56) References Cited

U.S. PATENT DOCUMENTS

| | | |
|---|---|---|
| 2008/0203080 A1* | 8/2008 | Fung ........................ A61F 7/034 219/212 |
| 2009/0149925 A1* | 6/2009 | MacDonald ............ A61F 7/034 607/96 |
| 2009/0198311 A1 | 8/2009 | Johnson et al. |
| 2011/0224760 A1* | 9/2011 | Potter ................... A61F 7/0097 607/104 |
| 2013/0006154 A1 | 1/2013 | Lowe |
| 2013/0172790 A1* | 7/2013 | Badawi ..................... A61F 7/02 601/15 |
| 2013/0172829 A1* | 7/2013 | Badawi ................ A61F 9/0008 604/294 |

* cited by examiner

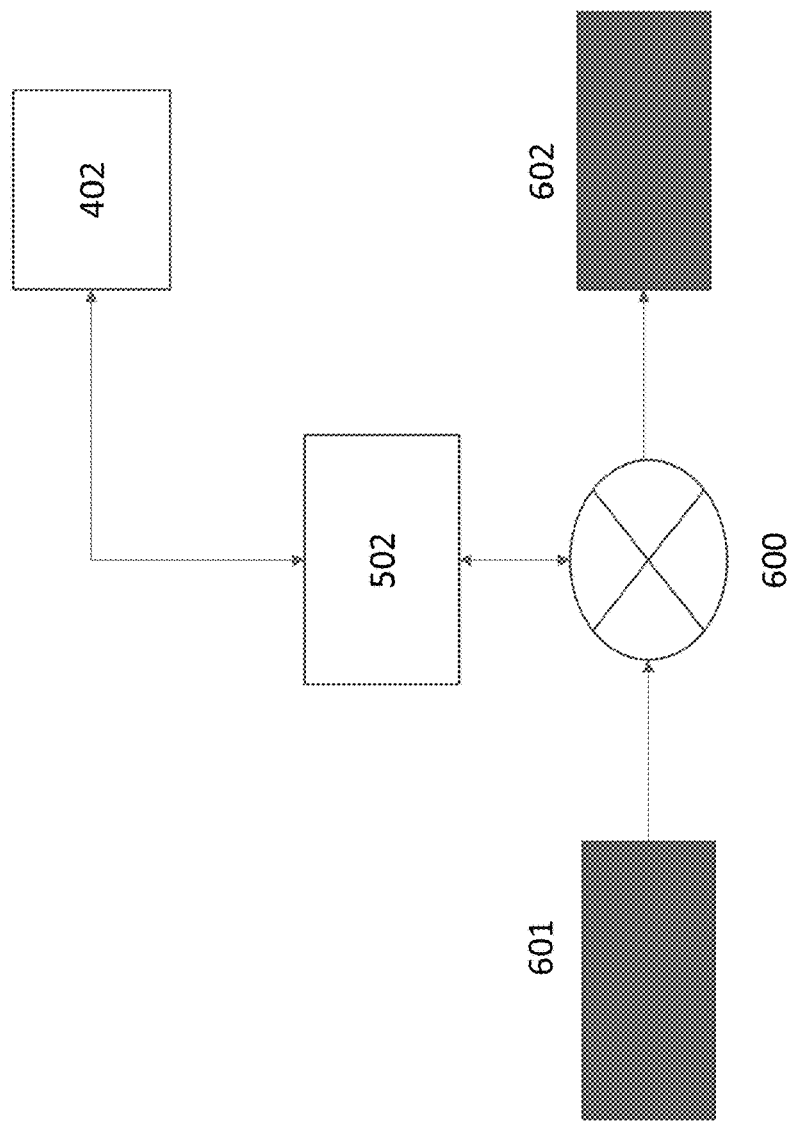

DISPOSABLE THERMAL REGULATION APPARATUS

CROSS REFERENCE TO RELATED APPLICATION

This application claims the benefit of U.S. patent application Ser. No. 61/770,895, filed Feb. 28, 2013, and U.S. patent application Ser. No. 61/845,136, filed Jul. 11, 2013, the entire contents of which are expressly incorporated by reference herein.

FIELD OF THE INVENTION

This invention relates to a disposable skin thermo-regulation apparatus for use by a medical patient. In particular, the present invention is directed to a covering to be worn over the scalp by patients undergoing chemotherapy. Specifically, the present invention possesses multi-chambered compartments for containing reactants, when combined, produce a chemical reaction designed to alter the temperature of the scalp or other portion of the anatomy.

BACKGROUND AND PRIOR ART

Breast cancer, and other forms of cancer, can be effectively treated in some cases by the administration of chemotherapy drugs such as Epirubicin, Docetaxel and Adriamycin. However, one side effect of this drug regimen is therapy induced alopecia.

It is known in the art that a hypothermia cap may be employed to prevent or reduce alopecia in chemotherapy patients. For example, it is known in the art that a hypothermia cap may be worn to induce local vasoconstriction around hair follicles during peak plasma concentrations of chemotherapeutic agents. Without being limited to any particular theory or mechanism or action, it is theorized that the decreased blood flow around the hair follicle lessens or prevents the impact of alopecia-inducing chemotherapy toxins, thus preserving the follicles, and ultimately, the patient's hair. Scalp cooling has been shown effective in reducing alopecia caused by anthracyclines and taxanes, but not when the two are used in combination.

Cooling the scalp to a temperature of +17° C. to achieve a subcutaneous temperature of +20 C (68° F.) constricts the blood supply to hair follicles diminishing or abolishing their perfusion. Thus the high chemotherapy dose delivery during the initial phase of chemotherapy is prevented from damaging the follicles. Further, coldness itself reduces the availability of (chemotherapy) cytotoxic drugs to the cells of the hair follicles by directly reducing their metabolic rate. It is the combined effect of both these mechanisms, induced by cooling the scalp that prevents or reduces hair loss (alopecia).

Currently, the prior art provides a number of arrangements designed to alter the scalp temperature of a patient. For example, U.S. Pat. No. 6,962,600, herein incorporated by reference, discuses the use of a cap device to cool the scalp. However, the device described requires the use of a non-disposable liquid coolant system.

U.S. Pat. No. 7,008,445, herein incorporated by reference, also describes a device for cooling the scalp. However, as seen, the device requires a significant investment in machinery. Furthermore, the system is not disposable.

Likewise, U.S. Pat. No. 7,052,509, herein incorporated by reference, describes a system for rapidly inducing hypothermia. Like the other cited prior art, the device in question is not suitable for a disposable arrangement.

Thus, what is needed in the art is a device for cooling the scalp of a patient that is disposable or easily replaceable. Furthermore, there is a need in the art for a device that does not require extensive mechanical linkages or ancillary apparatus.

SUMMARY OF THE INVENTION

In light of the foregoing, and in no way limited to the specifics herein, it is an object of the present invention to provide a cooling apparatus which provides a disposable thermo-regulation apparatus to be used on the scalp, or another area in need of vasoconstriction. Specifically, the present invention is directed to a cap or other headgear that allows for the device to come into contact, or otherwise cool or warm the scalp. In one example, the thermo-regulation cap is equipped with a number of cells, each cell containing the reactants for an endothermic or exothermic reaction. Upon mixing the reactants, the endothermic or exothermic reaction takes place and cools or warms the wearer's scalp.

In broad overview, the thermo-regulation cap is designed to reduce the surface and subcutaneous temperature of the wearer. Furthermore, through the use of endothermic chemical reactions, the thermo-regulation cap is disposable and portable. In addition to use by chemotherapy patients, the present invention is useful in headache and fever relief. The invention is configurable for use by paramedics and hospitals in head traumas to reduce swelling and bleeding: hypertensive encephalopathy, and other medical conditions and indications such as but not limited to inflammatory pathology such as meningitis, encephalitis, sinusitis, TMJ, hypertensive headaches, neoplasm, vasculitis and the like.

BRIEF DESCRIPTION OF THE DRAWINGS

The foregoing and other features of the present invention will be more readily apparent from the following detailed description and drawings of an exemplary arrangement of the elements of the device described in which:

FIG. 5 illustrates a further arrangement of the thermo-regulation apparatus according to FIG. 4.

DETAILED DESCRIPTION OF THE INVENTION

By way of overview and introduction, the present invention is directed to a cranial thermo-regulation cap configured to be portable and disposable.

Those skilled in the art will appreciate that the present thermo-regulation device is suitable for a number of configurations and arrangements. The device illustrated in the accompanying figures is designed for use as a scalp covering. However, the present invention is adaptable to a variety of arrangements and configurations to suit any number of goals which are in keeping with the functions of the present invention.

Figure 1:
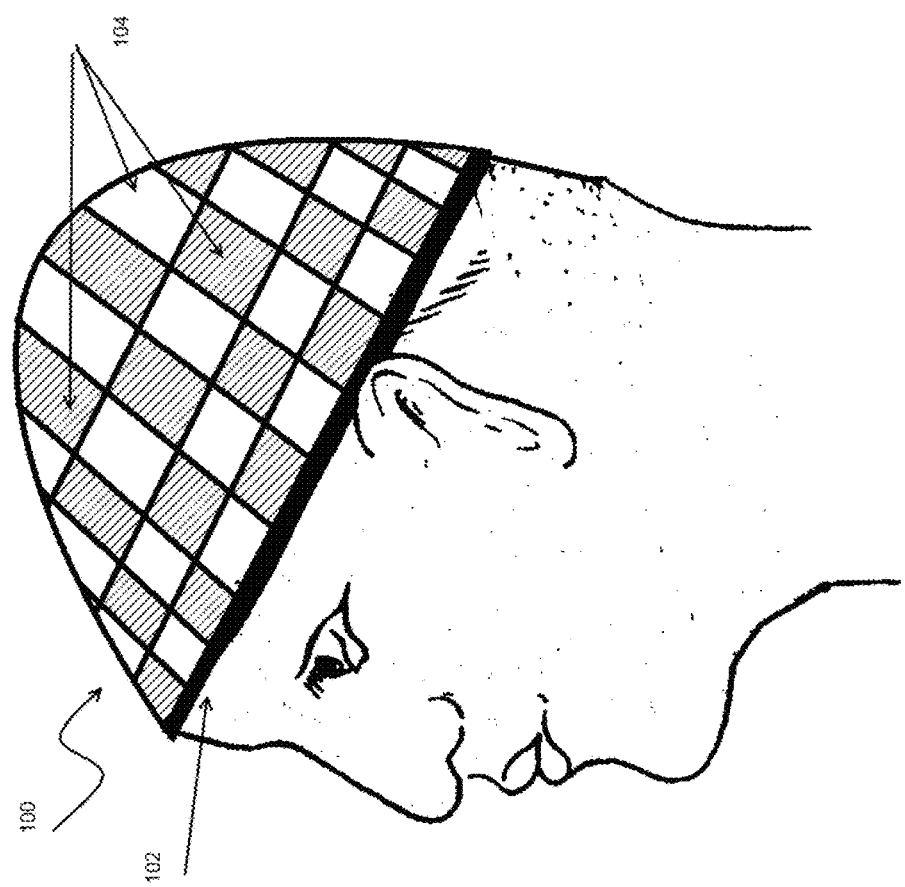
FIG. 1 illustrates a side view of a particular embodiment of the thermo-regulation apparatus according to the present invention.

As seen in FIG. 1, a thermo-regulation cap 100 is provided. Those skilled in the art will appreciate that the dimensions and styling of the depicted device is for clarity and ease of description. The present invention can be formed, depending on preference and necessity, in a variety of shapes and sizes. As such, the form of the cap depicted is only an example and does not limit the present device to a particular configuration.

The cap is configured to enclose the scalp. In the illustrated arrangement, the cap is configured with an elastic or conformable band 102 that produces sufficient tension to secure the cap to the user. The cap is formed of any suitable material. For example, the cap is formed of plastic, synthetic, natural or other fibers or sheets. In the illustrated arrangement, the cap is formed of a plastic material having heat retention properties.

The cap 100 in the illustrated arrangement is equipped with cells 104. Each cell in the illustrated configuration spans the width of the cap. However, in alternative arrangements, the cells are formed as smaller discrete cells. In one arrangement the cells 104 span the surface of the cap in a single layer. In an alternative arrangement, the cells 104 of the disclosed apparatus are arranged in a honeycomb or three-dimensional lattice. In the configured arrangement the cap can be secured to clothing, or itself, by fasteners, clamps, clasps, zipper arrangements and adhesive tabs.

Figure 2:
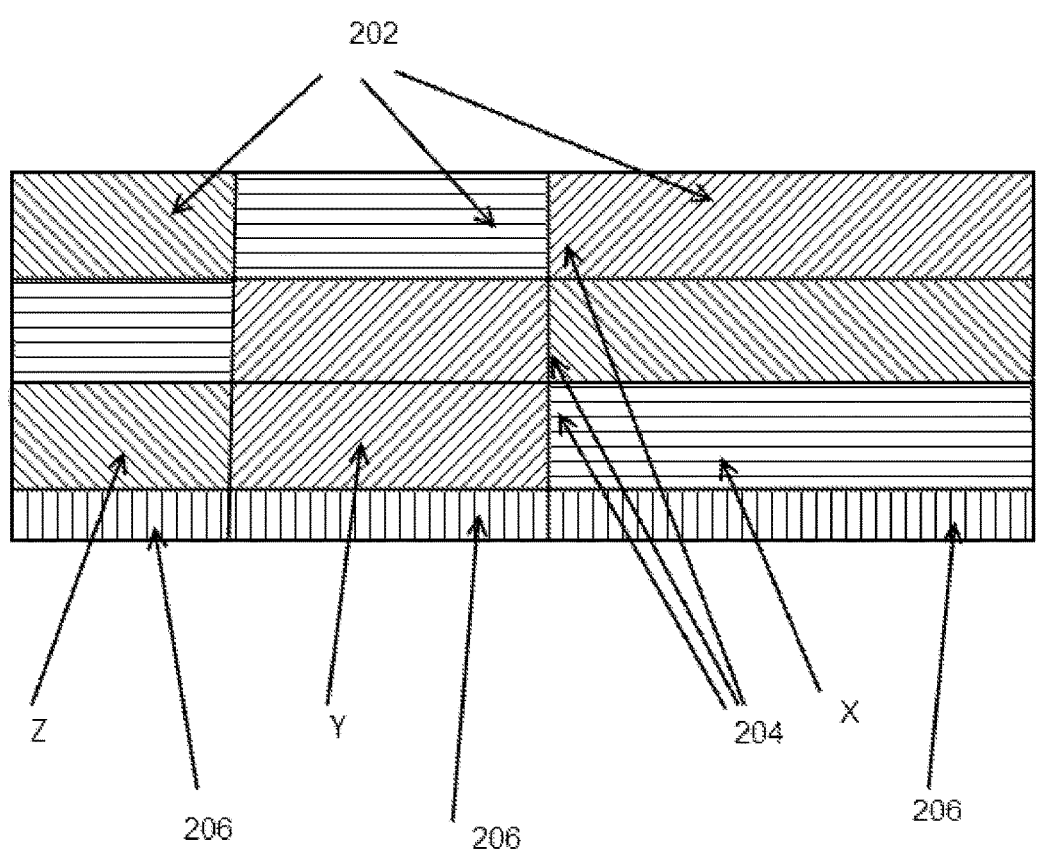
FIG. 2 illustrates a cross-section view of the thermo-regulation apparatus according to the device of the present invention.

As shown in FIG. 2, the cells of the present illustration are provided in series of layers, so as to achieve a 3-dimension arrangement of cells 202. In the depicted arrangement, the cells 202 are equipped to contain an assortment of reactants (X, Y, Z). Through combining the reactants, the endothermic or exothermic reaction is triggered. For example, and in no way limiting, the cells 202 of the present invention are filled with barium hydroxide octahydrate crystals or dry ammonium chloride. In this arrangement, the two reactants are separable by a breakable barrier 204. Upon breaking the barrier 204, at least two of the reactants mix and the reactions are triggered. In one arrangement, the breakable barrier 204 is broken by flexing, twisting, or otherwise physically dislocating the barrier 204 separating the reactants. Furthermore, in an alternative arrangement, the reactants are manually mixed by agitating the entire device, i.e. by shaking, after the device has been flexed.

In a further arrangement, the device is equipped with a plurality of cells, where each cell is equipped to contain at least two sequestered reactants. The sequestered reactants are separated by a destructible barrier and are configured to produce a chemical reaction when combined with at least one other reactant contained within the cell.

In this arrangement, individual cells are configured to deliver thermo-regulation. Such that a targeted thermo-regulation could take place.

In the alternative, the thermo-regulation cap is provided with a grid or array of receptacles configured to receive a removable cell. In this configuration each cell is configured to contain at least two reactants that when combined produce a chemical reaction. The removable cells in the described arrangement also include a thermo-regulation layer for making contact with the skin of an individual. In this configuration, the cell is placed at a specific grid coordinate determined to be a location on a body where thermo-regulation is desired. In this arrangement, a plurality of cells is placed in differing grid locations to allow for simultaneous treatment of various locations over the body without the necessity of thermo-regulation the entire area.

Additional examples chemical reactions are also envisioned. For example, an endothermic reactions involving ammonium chloride and water; thionyl chloride ($SoCl_2$) and cobalt (II) sulfate heptahydrate; water and ammonium nitrate; water with potassium chloride; or reacting ethanoic acid with sodium carbonate are all envisioned. Likewise the oxidation of iron, calcium oxide and water, copper sulfate and zinc and other exothermic reactions are also envisioned. Applicant does not limit the function of the present invention to these specific examples. Those skilled in the art appreciate that any endothermic reactions that are suitable for the purposes described can be used with the present invention.

As further seen in FIG. 2, the device illustrated also is equipped with a thermally conductive layer 206. In the described configuration, during an endothermic reaction, the thermally conductive layer provides for an averaging of the temperatures across the scalp.

Figure 3:
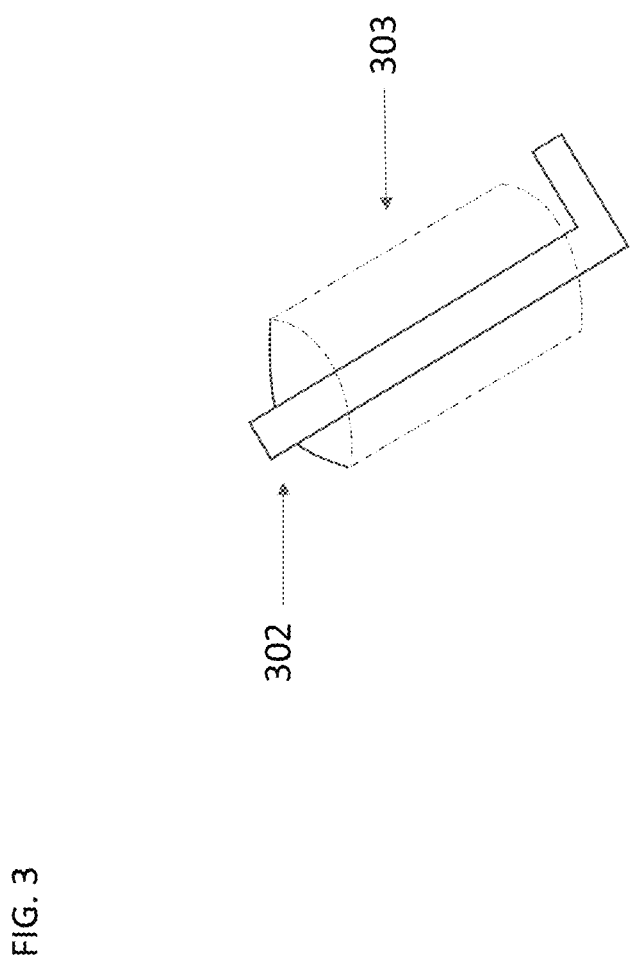
FIG. 3 illustrates a further arrangement of the thermo-regulation apparatus according to FIG. 1.

As seen in FIG. 3, the present invention is configurable in a variety of different formats. For example, the device described can be used as a sleeve or jacket 303 for encircling a limb or appendage 302. In the illustrated configuration, the present device is formed as a sleeve 303. A limb 302 in need of thermal regulation is inserted into the sleeve 303. In the illustrated configuration, the endothermic reaction is triggered as described above.

Figure 4:
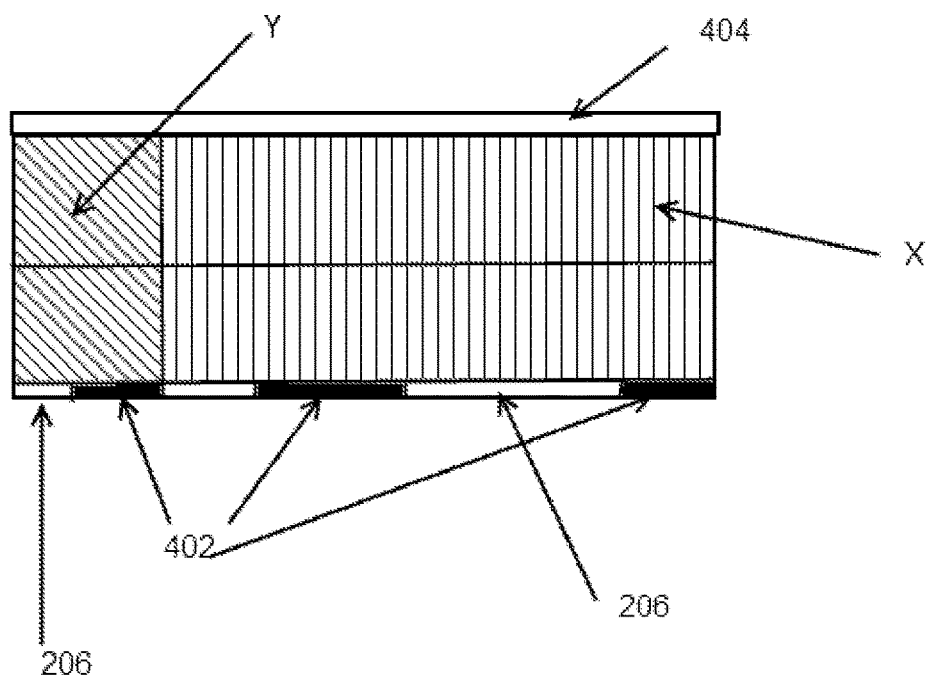
FIG. 4 illustrates a further arrangement of the thermo-regulation apparatus.

FIG. 4 illustrates the device equipped with a plurality of thermal monitoring devices 402. For example, thermocouples or other electronic temperature sensing devices are arrayed throughout the device 100. In this configuration, the temperature sensors are designed to detect the temperature levels and alert a user if the levels become a concern. The temperature sensors are integrated in to the thermally conductive layer. 206 Additionally, the device described is coated with a thermally reactive material 404 on the portion facing away from the user. The reactive material 404 alters its color depending on the temperature. Through this arrangement, a color coded indicator describing the appropriate temperature range is provided to a user.

In FIG. 5, the device described is configured with a microprocessor 502. The microprocessor 502 is connected using RF or EM (modulated electromagnetic signal) frequencies (for example, WI-FI, BLUETOOTH, RFID, NFC, or IR transducers, and the like) to transmit temperature information to a central database or storage device (not shown). In a further arrangement, the device is in communication with a portable computer device 504, such as a smart phone, configured to run executable code. In this configuration, the smart phone 504 provides monitoring of the temperature of the device and also provides a timing element, used to indicate when the device should be removed.

In a further arrangement, the microprocessor 502 is configured to open a valve or direct a pump 600 to move at least one reactant from a reservoir 601 to a second reservoir 602 containing a second reactant. Furthermore, the microprocessor 502 is configured to move and direct reactants based on temperature sensors 402 embedded in the cap.

Once the device of the present invention no longer provides a thermo-regulation function, it is disposed of or recycled for future use.

In an alternative arrangement, the present device is configurable to generate heat for the treatment of medial ailments. For example, the individual cells, as described in FIG. 2, contain an exothermic compound that when mixed, or exposed to air, undergoes heating. This heating is then directed to the user or to a heat retention device that absorbs the heat and radiates that thermal energy to the user directly.

In an alternative, the device so described is equipped with thermal-couple devices configurable to generate heat and direct that heat to warm a user or provide thermal therapies. In an alternative, the device so described is equipped with thermal-couple devices configurable to generate cool and direct that heat to warm a user or provide thermal therapies. In a further configuration, the microprocessor is configured to control the activation of the thermal couple devices.

In one arrangement, the thermal couple devices are supplied by an external power source. Alternatively, the thermal couple devices are supplied with an on-board or portable power supply.

It should be understood that various combinations, alternatives and modifications of the present invention could be devised by those skilled in the art. The present invention is intended to embrace all such alternatives, modifications and variances that fall within the scope of the appended claims.

While the invention has been particularly shown and described with reference to a preferred embodiment thereof, it will be understood by those skilled in the art that various changes in form and details may be made therein without departing from the spirit and scope of the invention.

Further objects and advantages of this invention will be apparent from the foregoing proposed arrangement of elements.

What is claimed:

1. A scalp covering device body, configured to provide a customized fit to the scalp of a user, the scalp covering device having an array of receptacles distributed across the scalp body so as to correspond to different portions of the anatomy of the user, each receptacle is configured to receive at least one removable cell and permit at least a portion of the received removable cell configured with a thermo-regulation material to make contact with the skin of a user when the cell is received in one of the array of receptacles, each removable cell having:
   one or more temperature sensors integral to the thermally conductive scalp covering body layer and configured to measure the temperature of the user facing surface;
   a first reservoir containing a first reactant,
   a second reservoir containing a second reactant, wherein the second reservoir is communicatively coupled to the first reservoir so as to permit the passage of the first reactant into the second reservoir,
   a reactant pump disposed between the first and second reservoirs and configured to pump the first reactant from the first reservoir to the second reservoir;
a microprocessor in communication with at least one of the one or more temperature sensors and configured to receive temperature information from the one or more temperature sensors, and further configured in communication the reactant pump, wherein the microprocessor is configured to control the activation of the reactant pump based on the measurements received.

2. The device as recited in claim 1, wherein,
the microprocessor is configured to communicate with a wireless communications device and transmit at least temperature data obtained from one or more temperature sensors to a remote server.

3. A scalp covering device comprising:
a thermally conductive scalp covering body having a user facing surface configured to conform to the scalp of a user,
one or more temperature sensors integral to the thermally conductive scalp covering body layer and configured to measure the temperature of the user facing surface;
a first reservoir containing a first reactant,
a second reservoir containing a second reactant, wherein the second reservoir is communicatively coupled to the first reservoir so as to permit the passage of the first reactant into the second reservoir,
a reactant pump disposed between the first and second reservoirs and configured to pump the first reactant from the first reservoir to the second reservoir;
a microprocessor in communication with at least one of the one or more temperature sensors and configured to receive temperature information from the one or more temperature sensors, and further configured in communication with the reactant pump, wherein the microprocessor is configured to control the activation of the reactant pump based on the measurements received.

4. The scalp covering device as recited in claim 3 wherein,
The first and second reactants, when combined produce an endothermic reaction.

5. The scalp covering device as recited in claim 3 wherein,
The first and second reactants, when combined produce an exothermic reaction.

* * * * *